(12) United States Patent
DeBrouse (10) Patent No.: US 6,397,106 B1
(45) Date of Patent: May 28, 2002

(54) APPARATUS FOR DESTROYING PATHOGEN MOLECULES USING FREQUENCIES

(76) Inventor: Joseph Wayne DeBrouse, 651 Billy B Rd., Louisa, VA (US) 23093

( * ) Notice: Subject to any disclaimer, the term of this patent is extended or adjusted under 35 U.S.C. 154(b) by 0 days.

(21) Appl. No.: 09/240,023

(22) Filed: Jan. 29, 1999

Related U.S. Application Data (60) Provisional application No. 60/073,311, filed on Jan. 29, 1999.

(51) Int. Cl.$^7$ ............................ A61N 1/00; A61M 21/02
(52) U.S. Cl. ............................ 607/69; 600/26; 600/28
(58) Field of Search ............................ 607/76, 68, 2, 607/69; 600/26–28

(56) References Cited

U.S. PATENT DOCUMENTS

| | | | |
|---|---|---|---|
| 4,919,139 A | | 4/1990 | Brodard ........................ 128/421 |
| 5,562,717 A | * | 10/1996 | Tippey et al. .................. 607/41 |
| 5,851,223 A | * | 12/1998 | Liss et al. ..................... 607/46 |
| 5,925,071 A | * | 7/1999 | Story ........................... 607/72 |

* cited by examiner

Primary Examiner—Kennedy Schaetzle
(74) Attorney, Agent, or Firm—Sheldon H. Parker (57) ABSTRACT

The frequency transfer system modulates square wave frequencies from a data storage medium to a pair of electrically conductive contact surfaces. The system contains at least one feed line into a transfer unit that has at least one voltage threshold limitation member to prevent the voltage from exceeding a predetermined amount. An anode and cathode leads terminate at the contact surfaces. A voltage indicator within the transfer unit is activated at a predetermined minimum voltage. The storage medium contains the odd harmonics derived from the square waves that are recorded in synchronization with the square waves. Body affixing means are used to maintain at least one of the contact surfaces with the a user's skin. Alternatively, the first contact surface contacts the user's skin and the second contact surface is proximate the user's skin. In one embodiment the data storage medium is a CD and is played through an amplifier placed between the CD player and the transfer unit. The minimum voltage levels are set through an amplifier in response to a prerecorded data storage medium that generates an optimum square wave amplitude. It is the combination of the square waves and odd harmonics of the square wave that provide the maximum benefit.

7 Claims, 5 Drawing Sheets

APPARATUS FOR DESTROYING PATHOGEN MOLECULES USING FREQUENCIES

RELATE BACK

This application is a continuation-in-part of U.S. application Ser. No. 60/073,311 filed Jan. 29, 1999, the contents of which are incorporated herein as though recited in full.

BACKGROUND OF THE INVENTION

1. Field of the Invention

An inexpensive, portable apparatus, and CDs, to enable frequencies to be played from a home CD player is disclosed.

2. Brief Description of the Prior Art

It has long been known that all substances are composed of atoms, each with a vibrational frequency inherent in its composition. Just as all substances have a vibrational frequency which maintains their integrity and composition, interference with this frequency can destroy the substances integrity. This can be seen when a singer has sufficient power in their voice to bring the frequency of the sung note to the frequency of a crystal glass, thereby breaking the glass. This physical law can also be applied to the icosahedral and helical symmetry within a cell. The amplitude of a vibrational frequency can disrupt a cell, destroying the protein bonds. Viruses and other pathogens are weakly bonded and their symmetry can be considered a torsional oscillator which can be destroyed by over driving these "oscillators" at their resonant frequency.

Once the ability to detect and measure the vibrational frequencies was discovered, the destruction of pathogens was explored. This is reflected in vast amounts of prior art and publications since the 1940s. Publications such as The Rife Way 3, Mark Simpson; Blast It, Part 2: Frequency Listings for Diseases, Disorders and Other Pesky Problems, Compilation Halal Information, Texas; and The Cure for All Diseases, Hulda R. Clark, PhD, MD, New Century Press, San Diego, Calif. (1995). The use of frequencies as a muscular therapy device is disclosed in U.S. Pat. No. 4,919,139 issued to Brodard. The device, however, consists of a computer and electrodes and requires complex programming to sequence the programmed pulses. Other patents have utilized frequencies, pulses and voltages; however, none have taken the frequency of specific pathogens, recorded the frequency, and made this treatment available in a compact, inexpensive system.

Without the ability to easily bring this technology to individuals, the full benefits are difficult to achieve. The disclosed invention makes the benefits of this technology easily accessible to the public. Additionally, the disclosure takes the relationship between the square wave created by audible sound and the subsequent cascading harmonics and converts this relationship to mathematical formulas. By making this relationship computable, subsequent identification of harmonics destructive to pathogens will be easier to define.

SUMMARY OF THE INVENTION

The disclosed system utilizes a recording medium which has been prerecorded with at least one specific frequency. The square wave frequencies are recorded resulting in sine wave harmonics which disrupt the molecular bond of the pathogen protein molecules. In one embodiment, a frequency transfer unit is disclosed that enables the user to play the prerecorded frequencies on existing stereo equipment. In this embodiment, the frequency transfer unit enables easy amplitude adjustment, through use of the stereo volume control, based on a specifically recorded set up CD. In another embodiment, the prerecorded medium is included within the vibrational unit to allow for portability. The vibrational unit contains electrodes which are affixed to opposing extremities of the body. The voltage received through these electrodes is in the 5–10 volt range.

Also disclosed is the mathematical calculations which allow the sine waves of inaudible frequencies to be reduced to audible square waves. The square waves generate sine waves at cascading odd harmonics which also facilitate the destruction of pathogens The frequency transfer system modulates square wave frequencies from a data storage medium to a pair of electrically conductive contact surfaces, such as stainless steel. The system contains at least one feed line into a transfer unit that has at least one voltage threshold limitation member to prevent the voltage from exceeding a predetermined amount. An anode lead terminating at a first contact surfaces and a cathode lead terminating at a second contact surfaces exit the unit. A voltage indicator within the transfer unit is activated at a predetermined minimum voltage. In one embodiment the voltage threshold limitation member can have a high and low setting to enable the maximum voltage to be varied.

The storage medium further contains the odd harmonics derived from the square waves and are recorded in syncronization with the square waves. Body affixing means are used to maintain at least one of the contact surfaces with the a user's skin. Alternatively, the first contact surface contacts the user's skin and the second contact surface is proximate the user's skin.

The square wave frequencies are created on a frequency counter/generator for storage on the data storage medium. In one embodiment the data storage medium is a CD and is played through an amplifier placed between the CD and the transfer unit. The minimum voltage levels are set through an amplifier in response to a prerecorded data storage medium that generates an optimum square wave amplitude.

The transfer unit can alternatively have a set switch with at least three positions. The first position placing the voltage threshold indicator in a mode to indicate the predetermined minimum voltage, a second position enabling modulation and flow of the voltage and a third position turning unit off.

Other embodiments can include a oscilloscope to monitor the square waves and/or a multimeter to monitor the voltage. A timer can be included that displays the time on a display screen, as well as time period buttons, for setting a period of time to play the data storage medium.

In one embodiment a securing pad is attached to the transfer unit. The securing pad has a first and second side, with the first contact surface embedded within the pad and positioned to be in contact with the user's body. A second contact surface is on the second side of the securing pad. When the user lies on the pad, electrons enter the user's body from the second contact surface and transfer through the user's body to the first contact surface.

In another embodiment the system uses a cathode pad, containing the second contact surface, in combination with a retaining member that contains the first contact surface. The user sits on the cathode pad and places the retaining member in contact with their skin.

It is the combination of the square waves and odd harmonics of the square wave that provide the maximum benefit.

BRIEF DESCRIPTION OF THE DRAWINGS

The advantages of the disclosure will become more apparent when read with the specification and the drawings, wherein.

DETAILED DESCRIPTION OF THE INVENTION

The disclosed technology has taken this known and proven scientific data further by amplifying the odd harmonics that naturally occur within the square wave.

The sine wave is the most common sound occurring in nature. A fundamental sine wave produces even and odd harmonics which are multiple frequencies of the fundamental. Therefore a 100 cycle per second sine wave produces harmonics of 200, 300, 400, 500, etc., cycles per second. The 100 cycle per second square wave, however produces only odd harmonics, 300, 500, 700 cycles per second and up.

It is the odd harmonics generated from a square wave that induce resonance in a body that sympathetically vibrates at the same, or nearly the same, frequency. The disclosed recorded medium, modulated by the frequency transfer unit, incorporates the square wave and its harmonic components. This applied resonance may either stimulate a cell to a higher energy state or it may destroy the cell if its amplitude (height of the wave) and time of application (duration) are sufficient.

The higher energy states can be enhanced to stimulate a cell into a sympathetic resonance more effectively. When this increased resonance exceeds the molecular bonding capability of the cell, the cell breaks apart destroying the organism. Consequently, what is experienced by the client is a local and/or general reaction of the immune system that can now recognize and eliminate the particulate matter as a result of the cells destruction. Somehow these insidious organisms that cause premature aging and our early demise appear harmless to our immune system until they are exposed to their resonant frequency and obliterated enabling the bodies defense mechanism to respond. This process is called a Die Off reaction. The Die Off reaction will continue to occur upon successive treatments until there are no longer enough degenerative cells to stimulate an acute immune response, or until there are no more cells remaining that are sympathetic to the frequencies being applied. Further advantages can be obtained from the disclosed device by periodically screening for a variety of potential degenerative organisms before they have the opportunity to cause harm to the body.

The basis for the destruction of pathogens through frequency modulation is the weak protein bond between molecules, as illustrated in FIGS. 1A–C, with each overlap or intersection region for each protein molecule serving as a weak point. Using this weakness, in combination with increased amplitudes at the pathogen's frequency, even ultra low intensity (10–16 w/m2) standing waves can rupture these bonding regions. When exposed to its most stressful mechanical oscillation mode, the disintegration of a pathogen can be viewed through a microscope. To illustrate why the bonds are disintegrated, FIG. 1A illustrates an example virus capsid 10 using a ten-member protein clumping. In FIG. 1B a mathematical abstraction of the virus capsid 10 is portrayed with a focus on the oscillation of a single protein 12. As can be seen, the focused area is an ellipse having its major axis at the bonding region with the adjacent protein and its minor axis as the center of mass of the protein molecule. An elastic coupling extends along the major axis between the protein molecules. It is at the bonding region between the adjacent protein molecules that the pathogen is weakest. Additional information to corroborate the process, as well as specific frequencies, can be found in publications such as The Rife Way 3, Mark Simpson; Blast It, Part 2: Frequency Listings for Diseases, Disorders and Other Pesky Problems, Compilation Halal Information, Texas; The Cure for All Diseases, Hulda R. Clark, PhD, MD, New Century Press, San Diego, Calif. (1995); and papers published by Dr. Royal Raymond Rife, Appendix B, C, D, F and G. The Robert Cathey Research Source, A Physicist's View of Dr. Rife's Non-Drug Treatment Cure of Microbial Associated Diseases, Bary Wade, health Freedom News, August, 1994. These publications are incorporated herein as though recited in full.

Figure 1:
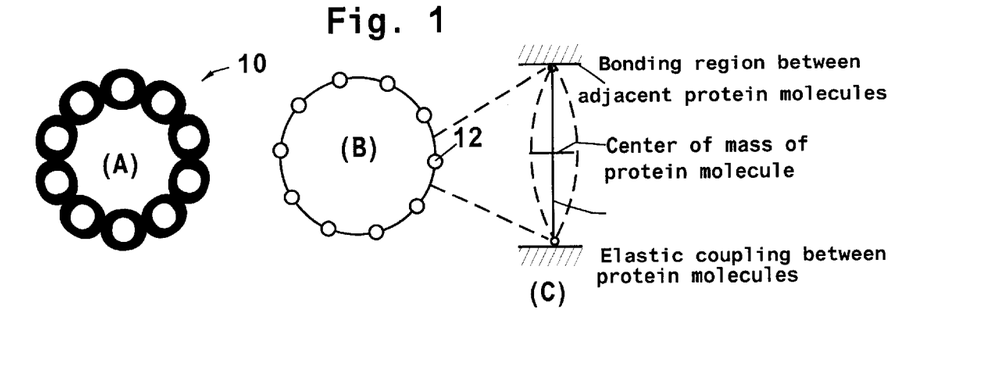
FIG. 1A shows a virus capsid protein molecule.
FIG. 1B is a mathematical abstraction of the virus.
FIG. 1C the bonding region, center of mass and elastic coupling of the protein molecule.

The theory disclosed by Dr. Royal Raymond Rife incorporates the following differential equation for free oscillation as shown in FIG. 1 of Appendix D:

$$d2S/dt2 + (b/m)dS/dt + Wo2S = 0;$$

where

S=displacement of the center of mass from the equilibrium position m=the mass of the protein molecule b=a positive drag factor constant Wo=the natural resonance angular frequency Thus, if m is displaced a distance from its equilibrium and released to freely oscillate, a displacement amplitude occurs. As can be seen, the amplitude of oscillation is exponentially decreased in time, due to the velocity-dependent drag force, represented by the magnitude of b. Additional equations for explaining Rife's view of this phenomena are found in his personal Appendix D, as cited above. Blast It! provides a sequence of Hertz frequencies, set forth below, which have been utilized by Rife and others in successful experiments. The applicable frequencies of specific diseases are also listed in subsequent pages of Blast It!.

As stated in the foregoing reference, an independent research group exposed a number of pathogenic microorganisms to the following frequencies, simultaneously, on a light carrier wave, killing the exposed microorganisms.

| 121 | 666 | 690 | 1840 | 1998 |
|---|---|---|---|---|

Further research in 1989 suggested the following frequencies

| 1 | 1.8 | 3.5 | 4 | 5 | 5.5 | 7 | 8 | 9 | 10 | 13 | 14 |
|---|---|---|---|---|---|---|---|---|---|---|---|
| 15 | 18 | 22 | 26 | 28 | 30 | 36 | 41 | 70 | 72 | 78 | 81 |
| 82 | 95 | 121 | 160 | 162 | 240 | 304 | 423 | 428 | 432 | 440 | 664 |
| 676 | 700 | 712 | 725 | 730 | 764 | 770 | 775 | 780 | 781 | 799 | 803 |
| 804 | 864 | 875 | 885 | 1000 | 1027 | 1050 | 1100 | 1550 | 1552 | 1862 | 1865 |
| 2050 | 2100 | 2120 | 2130 | 2180 | 2200 | 2452 | 2720 | 31000 | 31750 | 34750 | |

Data from hundreds of successful experiments found the following sequence of Hertz frequencies, as published in Blast It!.

| 1 | 1.8 | 3.5 | 4 | 5 | 5.5 | 7 | 8 | 9 | 10 | 13 | 14 |
|---|---|---|---|---|---|---|---|---|---|---|---|
| 15 | 18 | 20 | 22 | 26 | 28 | 30 | 36 | 41 | 60 | 70 | 72 |
| 78 | 80 | 81 | 82 | 95 | 100 | 120 | 121 | 125 | 160 | 162 | 240 |
| 250 | 304 | 400 | 423 | 428 | 432 | 440 | 450 | 465 | 500 | 600 | 622 |
| 625 | 650 | 660 | 664 | 666 | 676 | 690 | 700 | 712 | 725 | 727 | 728 |
| 730 | 740 | 764 | 770 | 775 | 776 | 780 | 781 | 784 | 787 | 799 | 800 |
| 802 | 803 | 804 | 864 | 875 | 880 | 885 | 1000 | 1027 | 1050 | 1100 | 1500 |
| 1550 | 1552 | 1560 | 1570 | 1600 | 1800 | 1840 | 1850 | 1862 | 1865 | 1998 | 2000 |
| 2008 | 2050 | 2093 | 2100 | 2120 | 2127 | 2128 | 2130 | 2180 | 2200 | 2250 | 2452 |
| 2489 | 2720 | 6500 | 5000 | 10000 | 31000 | 31750 | 34750 | | | | |

Although these frequencies were obviously known, they have not been widely used, partially due to equipment inconvenience. The equipment used by Rife, and others, was bulky and expensive, thereby requiring visits to a facility for each treatment. Conversely, the frequency transfer units disclosed herein enable this frequency technology to be easily accessible to anyone with a stereo or other medium, such as a computer CD, Walkman, etc. Although the frequencies for use with the transfer unit disclosed herein can be recorded on any recording medium, such as computer chip, tape, etc., for ease of description, reference will be made herein to the use of a CD and amplifier. Optimally, the recording medium is high quality and distortion free, with user selectable tracks.

Magnetic medium can be used; however, this medium is generally not distortion free, is easily destroyed, and does not have the track selectability of other mediums, such as a CD. Since the frequencies being used to break the pathogen bonds are modulated for a specific pathogen, the frequency output must be within 20% of the targeted frequency. To maintain effectiveness, the recording medium must have the ability to repeatedly reproduce the originally recorded frequencies. When a recording medium is of a size sufficient to be incorporated within the vibrational unit, such as a computer chip, the vibrational unit can serve as player and modulator.

The following definitions are used herein in a standard, industry accepted manner.

Fundamental wave: having the form of a series of curves or undulations. The length of the wave is determined by the frequency of its rise and fall in relation to time (cycles per second).

Frequency: The number of periodic vibrations express in cycles per second or Hertz (Hz).

Harmonic: A mathematical progression of frequencies naturally produced from a fundamental frequency (sine wave or square wave).

Resonance: The effect produced when the natural vibration frequency of a body is greatly amplified by reinforcing vibrations at the same or nearly the same frequency from another body.

Frequency Transfer Unit

The frequency transfer units disclosed herein provide the electronic liaison between the CDs and the user. Safety features, in the form of resistors and diodes, or the equivalent, prevent excessive voltage from reaching the user. If the directions for use are followed, the voltage transferred through the transfer units automatically adjusts to an appropriate level. However, if the user inadvertently increases the volume on the amplifier or fails to follow the set up directions, the unit prevents the higher voltage from reaching the user.

Figure 2:
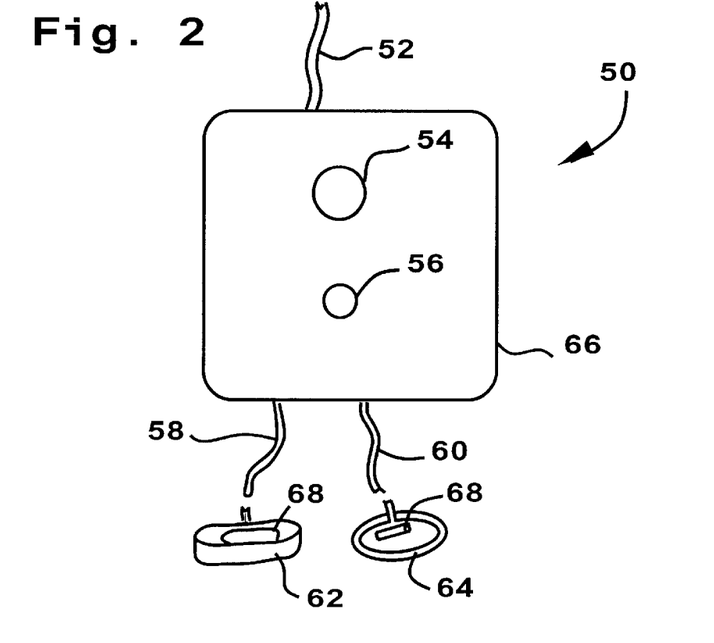
FIG. 2 is a front view of the exterior of the preferred embodiment of the disclosed frequency transfer unit.
Figure 3:
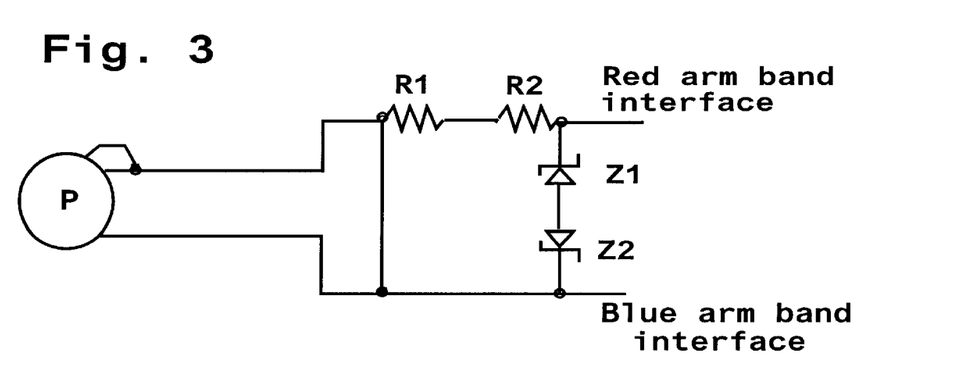
FIG. 3 is a schematic of one method of arranging the interior electronics for the unit of FIG. 2.

The preferred frequency transfer unit 50, illustrated in FIG. 2, has a body 66 containing the electronics, an example of which is illustrated in FIG. 3. An feed line 52 is configured to be connected to the user's stereo and provides the frequency input into the transfer unit 50. As illustrated, the feed line 52 is connected to the earphone port of the user's amplifier, however, other output ports can be used with appropriate equipment modifications, as will become evident to those skilled in the art.

Two output leads, cathode lead 58 and anode lead 60, exit the body 66 and are connected to electrode plates 68, which are in turn affixed to lead bands 62 and 64. As illustrated in FIG. 2, the cathode lead band 62 and anode lead band 64 are elasticized bands for placement on a user's wrist or ankle, however any method that securely places the electrode plates 68 against the skin can be used. The cathode lead 58 introduces the voltage to the user where it is "attracted" to the anode lead 64. To reach the anode lead 64, the voltage must travel through the user's body, thereby destroying cells attuned to the specific frequency being played on the CD.

One of the preferred material for manufacture of the electrode plate 68 is stainless steel, although other materials can be used. Stainless steel is an optimum material as it is non-allergic and does not produce "hot spots" within the plate. By maintaining even transference of the frequencies along the plate 68, the voltage output of the frequency transfer unit can be increased without any discomfort to the user, thereby increasing the effectiveness of the device. Other conductors, including composites, can be used providing they produce the same results as stainless steel.

The body 66 of the transfer unit 50 preferably contains an on/off switch 56, although the unit 50 can be turned on and off simply by unplugging the input line 52 from the amplifier and/or CD source. The addition of the on/off switch 56 is a matter of cost and manufacture and/or consumer preference. A setting light 54 is used to indicate that the appropriate number volts are entering through the feed line 52. The voltage acceptable by the user, and hence the unit, is determined and "enforced" by resistors and diodes installed at the time of manufacture. The output of the transfer unit should not exceed 11 volts, while 5 volts would be the minimum applicable output. Although the zenor diodes Z1 and Z2, as illustrated in FIG. 3, will prevent the voltage from going above the predetermined level, when a stereo amplifier is being used to drive the device, only visual recognition, via the volume control and setting light, can ensure that the voltage has reached the predetermined level. Other indicating signals, such as vibratory or audio, can replace the visual signal of the setting light 54. Alternatively, more than one indicating signal can be installed at time of manufacture and the desired signal, or combination, can be selected by the user.

To set up the frequency transfer unit for use, a setup CD is provided that enables the user to set the proper volume of the amplifier, bringing the recorded square waves to the appropriate amplitude. The set up CD is played while the volume on the amplifier is turned up to the point where the setting light 54 has just begun to pulse at 5.5 Hz. This is the proper amplitude at which recorded therapeutic protocols are viable. It should be noted, however, that these values can vary depending upon equipment. The user ceases turning up the volume at that point and replaces the set up CD with the appropriate frequency CD to be utilized for a therapeutic session.. The frequency transfer unit will continue to modulate the optimum square waves and recorded harmonics until the amplifier volume is decreased or turned off.

Figure 9:
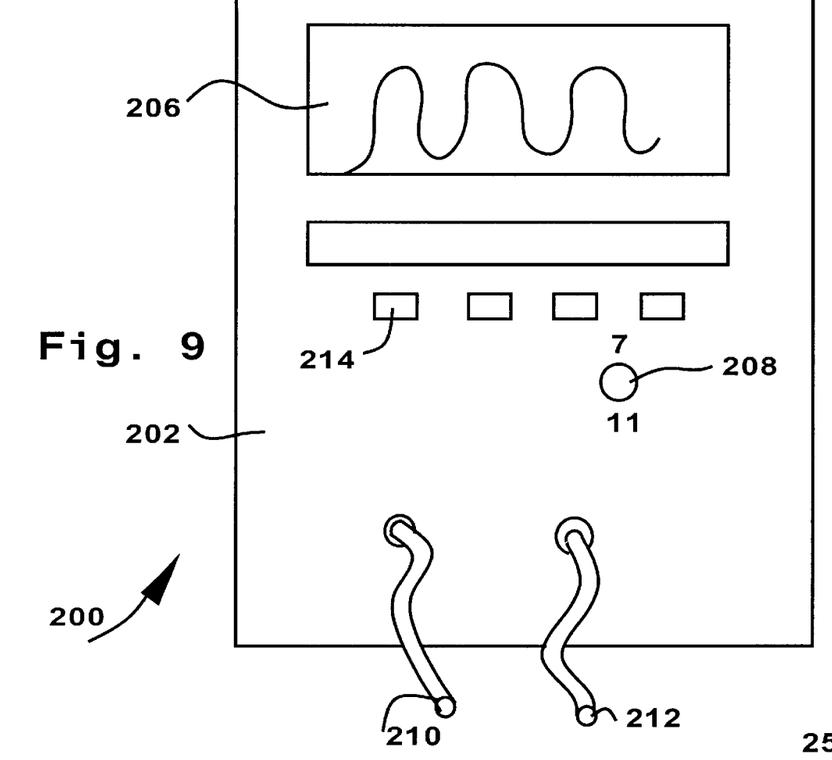
FIG. 9 is a front view of a amplifier/CD combination frequency transfer unit containing alternative voltage controls.

For units having an amplifier/CD combination, such as illustrated in FIG. 9, the minimum voltage will be automatically established and setting the minimum level is not required. The unit 200 does not require the equivalent of a volume setting knob as this is permanently set within the body of the unit. The unit can be provided with the normal CD functions buttons 214 such as play, repeat, etc.

It should be noted that the voltage references herein are within the safe range for humans. This technology can also readily be adapted for animal use and the voltage would necessarily require adjustment in accordance with the physiology of the particular animal.

Figure 4:
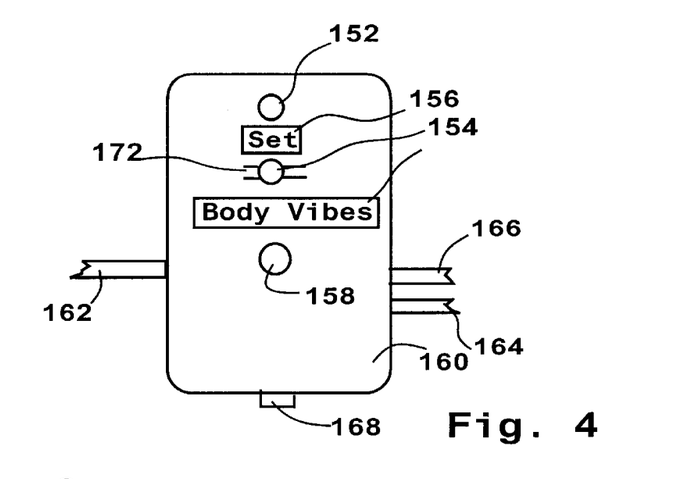
FIG. 4 is a front exterior view of an alternate embodiment of the frequency transfer unit.

In the embodiment illustrated in FIG. 4, the unit 150 has a feed line 162 that leads into the body 160 from the user's receiver. A cathode output line 164 and anode output line 166 exit the body 160 and end in an ankle electrode 180 of FIG. 6 and a finger electrode 186 of FIG. 7. Although the finger electrode 186 is illustrated as being connected to the cathode output line 164 and the ankle electrode 180 connected to the anode output line 166, this is only one embodiment and the cathode/anode lines can be switched as desired. The finger electrode 186 and ankle electrode 180 are, as stated heretofore, preferably manufactured from stainless steel to prevent "hot spots". Although stainless steel is preferable, other electrically conductive materials, such as composites, aluminum or copper, that transmit AC voltage corresponding to the recorded frequencies to the skin. The body 160 of the unit 150 is provided with an indicator 152, such as a red LED, a set switch 154 and an operating indicator 158, such as green LED. The indicator 152 and operating indicator 158 preferably provide distinctive indications, such as different colors, as each indicates an opposing function. Although the LEDs are referred to as red and green in the description herein, this is used for reference purposes and in no way limits the scope of the invention.

The 12-volt indicator 152 is used, in combination with the set switch 154, to enable the user to know when the proper voltage for the specific CD being played has been obtained. The illustrated set switch 154 is a three way switch which enables the unit 150 to be placed in the "set" position 156, "off" position 172 or the "operating" position 170. The operating indicator is used to indicate unit operation when the switch 154 is placed in the operating position 170. The incorporation of the three-way set switch additionally provides a neutral or "off" setting. For protection of the unit 150, a fuse 168, for example 63 milliampere, is preferably incorporated in line with the electronics within the unit 150. In the event the electrodes in this embodiment are manufactured from a non-flexible material, several sizes can be produced to enable the electrode to fit more than one finger or ankle size.

Figure 6:
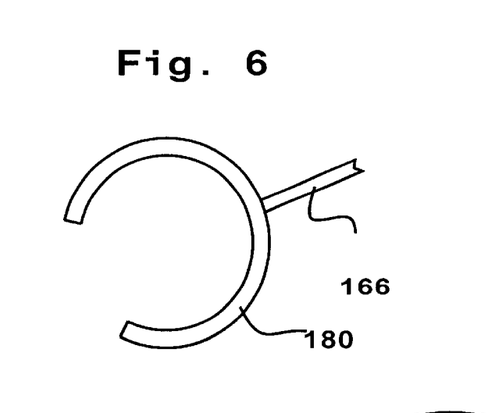
FIG. 6 is a side view of the ankle electrode for use with the frequency transfer units.
Figure 7:
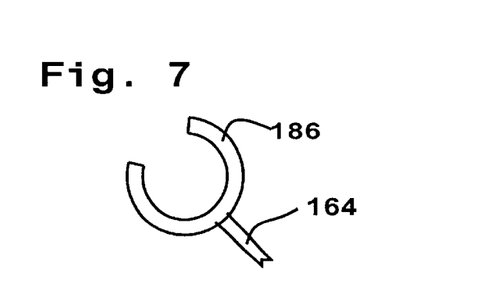
FIG. 7 is a side view of the finger electrode for use with the frequency transfer units.
Figure 8:
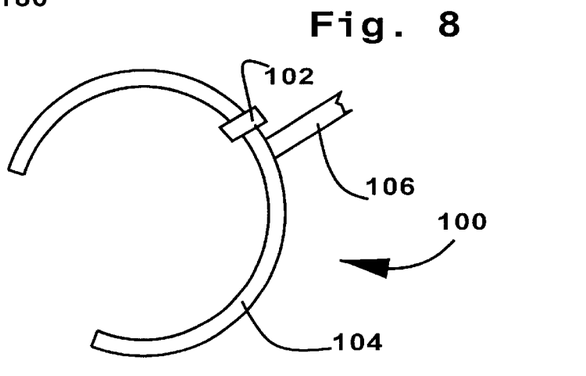
FIG. 8 is a side view of an alternate embodiment of an ankle electrode.

Alternatively, standard self-adhesive electrode pads, as commonly used with EKGS, can be used in combination with an electrolyte gel. Additionally, the electrolyte gel can be used with the foregoing electrodes 68, 180 and 186.

Figure 5:
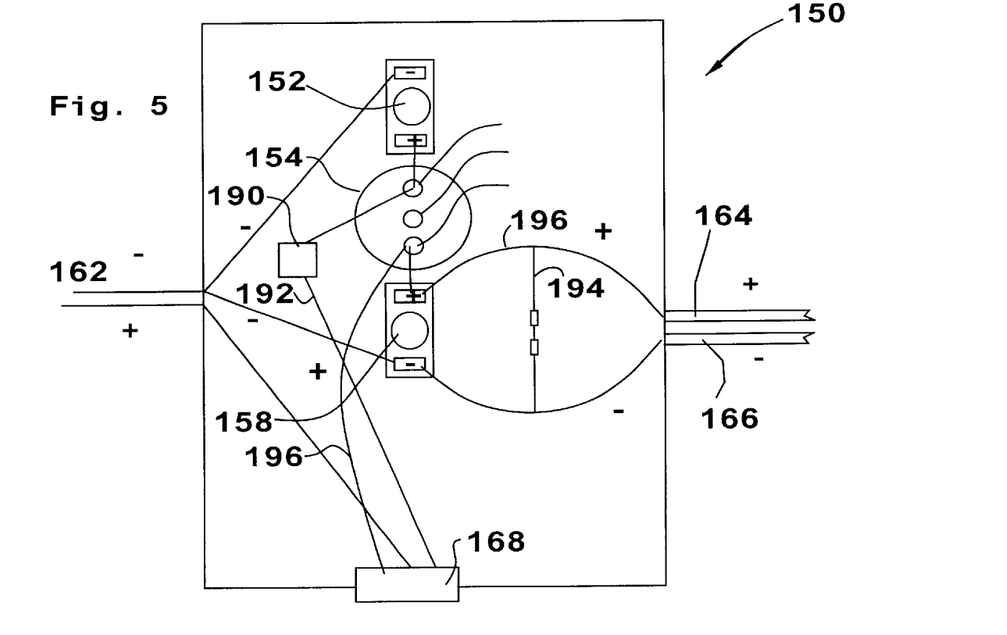
FIG. 5 is a schematic of one method of arranging the interior electronics of the unit of FIG. 4.

An alternate example of an interior electrical system is illustrated in FIG. 5. As can be seen, the feed line 162 is divided, with the positive wire going to the fuse 168 and the negative wire going to the negative connections on the indicator 152 and operating indicator 158. From the fuse 168, the positive line 192 is put into a transient voltage suppresser 190 prior to connecting to the switch 154 and red LED 152. The transient voltage suppresser 190 is optimally in the range of 13 to 16V, to attenuate the voltage going into the indicator 152. By placing the transient voltage suppresser 190 between in line with the indicator 152, a disparity is created between the indicator 152 and operating indicator 158. Since the indicator 152 is used to set the output through volume manipulation, the range of the indicator 152 needs to be greater than that of the operating indicator 158. When the switch 154 is in the set 156 position, the output voltage is partially attenuated while being diverted to the indicator 152. Once the switch 154 is placed in the off mode 172, the connection with the indicator 152 is broken. Placing the switch 154 into operating position 170, the connection with the operating indicator 158 is activated to maximum applicable output amplitude. Although a two position switch can also be used, it is preferable that the unit 150 have a center off position during which time the unit is inoperable.

To set the system prior to each application, the CD is placed into the player and the volume of the amplifier is turned down to the lowest level. In the event the unit 150 is not plugged into the speaker output, the speakers are switched off. Each CD, when initially produced, is recorded with a reference frequency as a first track. This reference frequency allows the user to align the volume of the equipment, and therefore the output voltage, with the prerecorded frequencies on the CD. To align the amplifier with the frequency, the switch 154 is placed in the set position 156. The volume on the amplifier is gradually increased until the indicator 152 begins to illuminate. The user should then slowly decrease the volume until the indicator 152 is just extinguished. The proper voltage is now set. The switch 154 is placed in the operating position 170 to establish full amplitude capacity to output electrodes, and the CD set to the desired tracks in the same manner as a standard CD.

An alternative ankle electrode 100, as illustrated in FIG. 6, is manufactured from a rigid material, thereby producing an inflexible body 104. A hinge 102 allows the electrode 100 to be opened and closed to fit snugly around the user's ankle. The hinge 102 is placed to avoid interference with the connection of the output line 106.

The ankle electrode 180 and finger electrode 186 are placed on the opposite extremities. It does not matter whether the electrodes 180 and 186 are placed on the right or left extremities, only that they are placed on the opposite extremities. The switch 154 is then placed in the operating position 170, thereby completing the connection.

In FIG. 9 a professional unit 200 is shown wherein the frequency transfer unit is incorporated, along with a multimeter 204 and oscilloscope screen 206, within the body 202. A voltage switch 208 is provided to take the voltage from a low to high point. Alternatively a knob can be provided to provide more than the two voltage settings. The cathode and anode leads 210 and 212 can be either plugged in using standard plugs, or permanently connected to the body 202. Preferably the unit includes an on off switch an a conveniently located area.

Figure 10:
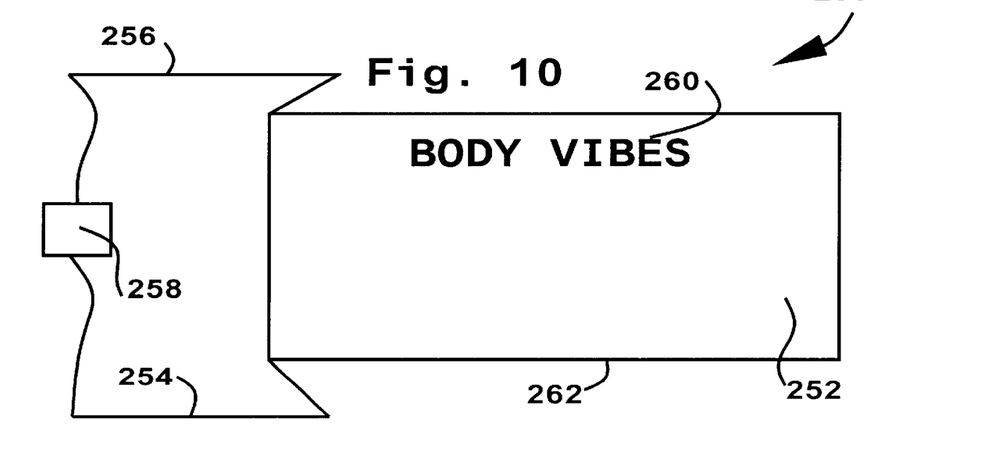
FIG. 10 is a partial view of a frequency transfer unit having the contacts placed on either side of a mattress pad.

FIG. 10 illustrates a bed unit 250 for use on a bed. The frequency pad 252 is placed across the bed mattress to come in contact with the user's body. The anode contact 260 is woven into the mat 252, in this embodiment in the words Body Vibes. The anode contact 260 must be in contact with the user's skin to attract the electrons from the cathode 262. The anode contact 260 is, in this embodiment, manufactured from a thin stainless steel, or silver, wire to provide comfort the user while providing maximum contact. If wire is used, the gauge will be dependent upon the end use. Alternatively, a thin, flexible solid plate can be substituted for the wire. The anode contacts 260 are then connected to the frequency unit 258 through use of anode 254. The cathode contact 262 is placed beneath the pad 252, facing the user. The cathode contact 262 is connected to the frequency unit 258 through use of the cathode lead 256. The electrons are transmitted from the frequency unit 258 to the cathode contact 262 beneath the pad 252. As the electrons are compelled to reach a balanced level, they are drawn to the anode contact 260, with the only way to reach the anode contact 260 being through the user's body.

Figure 12:
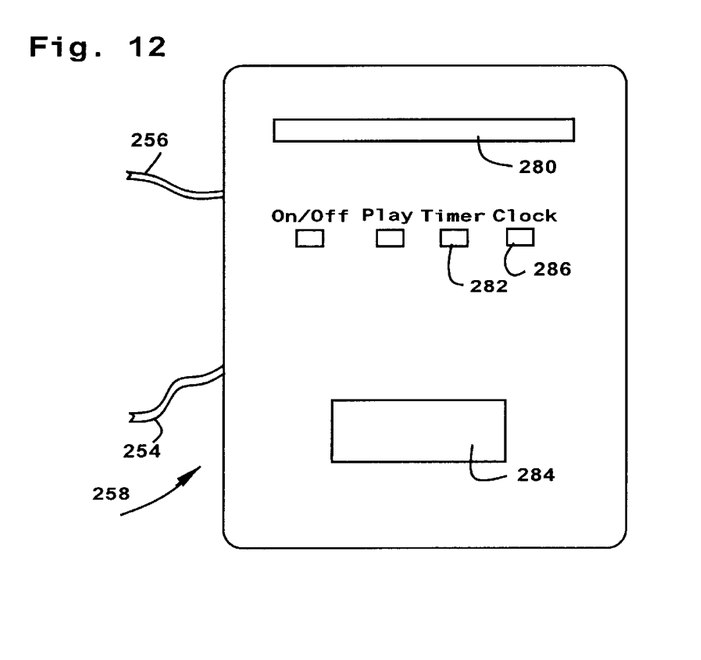
FIG. 12 is a front view of a frequency transfer unit containing a CD player/timer.

The frequency unit 258 illustrated in FIG. 12 enables the user to use the frequency unit 258 during sleep without any inconvenience. The frequency unit 258 has the amplifier and CD 280 built into the unit and, in addition to the standard on/off and play buttons, a display screen 284 and timer 282 and clock 286 set buttons are provided. The clock 282 would be set using standard minute/hour buttons. The timer 282 would set the period of time the CD player 280 would run. In this way, the CD could be used on a timed basis if desired. Alternatively, the timer can be set for an "on/off" time as known in the alarm art. This embodiment enables the user to preset the period of time required for the particular set of frequencies.

Figures 11, 13:
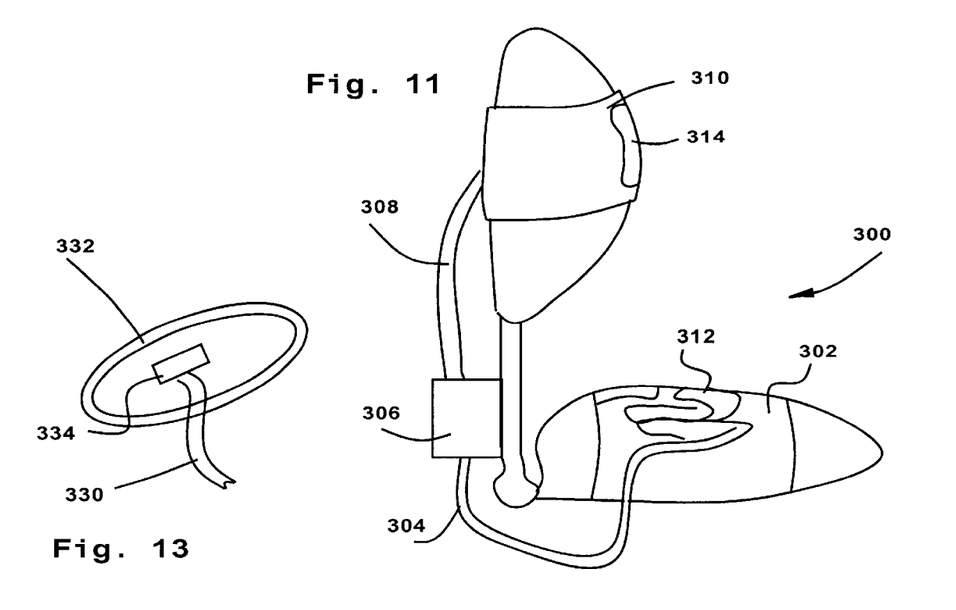
FIG. 11 is a perspective side view of a frequency transfer unit having the contacts placed on either side of an office chair.
FIG. 13 is a contact placed in a arm band for use with FIG. 11, to enable the contact to be placed proximate the skin of the user.

In a preferred embodiment, the player would be provided with "beginning set" and "end set" buttons to enable a block of frequencies to be repeatedly played for the predetermined time period. Once all of the blocks of sets are programmed in, the time for each set would be programmed. This enables a first set of frequencies to be played for a first period of time and a second and/or third sets to be played for different periods of time. In FIG. 11 the frequency unit 306 is removably affixed to a office chair 300, although this embodiment is also applicable to car seats, lounge chairs, etc. The seat pad 302 is wrapped around the chair 300 with the cathode contact 312 woven into the pad 302, as described in conjunction with FIG. 10. The cathode contact 312 is affixed to the frequency unit 306 through use of cathode lead 304. The anode contact 314 is placed on the back pad 310, as noted above, and connected to the frequency unit 306 through use of the anode lead 308. In order for the electrons to be attracted to the anode contact 314, the anode contact 314 must be in communication with the user's skin. In the embodiment illustrated in FIG. 11, the user's shirt would be moved to enable the communication between skin and contact 314. In office settings this would frequently create a problem and therefore a wrist or arm band 332 can be used rather than the pad 310. The elastic, or otherwise adjustable band 332 contains the anode contact 334 and is connected to the unit 306 through anode lead 330. The band 332 is placed around the user's arm, or wrist, to come in contact with the skin. Alternatively, the band 332 can be replaced by a belt or ankle band, or other device to secure the contact between the users skin and the electrode 334. Preferable the anode lead 308 unplugs from the frequency transfer unit 306 to enable easy substitution of additional anode contacts. Thus, a user can use the pad 310 at home or bring the unit into the office and plug in a wrist band contact.

The desired frequencies are placed onto the recorded modulating medium for a predetermined length of time and may be repeated as necessary to equal the recommended treatment time. The treatment time is dependent upon the pathogen and its severity, user body weight, etc. Since application of the frequencies for periods of time longer than the recommended time period cannot harm the individual, the concern is matter of insuring that the frequencies are used for a period of time sufficient to allow destruction of the pathogens' molecular bonds. As stated herein, the frequencies are not of an amplitude to penetrate and harm healthy cells. Only the pathogens residing at the outer portion of the tissues are destroyed by the frequencies with pathogens residing within the tissue migrating outward to occupy the empty spaces. The use of repeated treatments destroys pathogens as they migrate to the outer portions of the tissues until all pathogens have been destroyed.

As each frequency is aligned with the frequency of the pathogenic protein bond to be broken, only bonds which are affected by these frequencies are those specific targeted pathogens. Normal cells are prevented from being affected by the recorded frequencies by their inherent structure. A normal cell has a hexagonal and pentagonal periphery, a stronger molecular matrix, and a substantially higher mortal oscillation rate. The voltage required to affect a normal cell is in the range of 50 volts and the safeguards provided in the disclosed device prevent the voltage level from reaching even close to a harmful point. As stated heretofore, the frequencies of many pathogens have been known for years. To date, however, the prior art has only consisted of cumbersome and expensive equipment. This knowledge has been taken no further than the destruction of pathogens without looking at these frequencies as one part of an interactive network affecting our health. Many of the strands of the network are known; however, to date they have not been woven together. From musical theory it is known that notes progress up and down the major scale with mathematical relationship, repeating every 12th semi-tone. Each note repeated within the octave is 12 semi-tones above or below the note in previous or subsequent octaves. In nature, the earth has a frequency, known as the Schumann Resonance, of 7.9 to 8.1 hertz, and each color of the rainbow vibrates at a specific frequency, which is analogous to one of the seven notes on the scale. Each note of a C major scale when divided by 32, starting at middle C scale, is equal to the lowest equivalent note of the C scale beginning at 8.1 hertz as seen in Table I.

These sub-harmonic frequencies also correspond to human brain waves. The chakra system of Ayurvedic medicine also corresponds to color frequencies, an accepted fact in Eastern philosophy for centuries. The foregoing method can also be used to enhance chakra frequencies, which directly correspond to the musical major C scale in a variety of harmonious combinations, using the appropriately recorded CDs. When enhancing the chakras, the frequencies can be accessed via either sine wave audio applications or square wave for electromagnetic pulse applications. The following are also applicable to chakras.

TABLE I

| Chakra | Color | Hertz | Hertz | Color |
|---|---|---|---|---|
| 1 | red | 261.63 ÷ 32 = | 8.17 | red |
| 2 | orange | 293.66 ÷ 32 = | 9.17 | orange |
| 3 | yellow | 329.63 ÷ 32 = | 10.3 | yellow |
| 4 | green | 349.23 ÷ 32 = | 10.9 | green |
| 5 | blue | 392.00 ÷ 32 = | 12.2 | blue |
| 6 | indigo | 440.00 ÷ 32 = | 13.7 | indigo |
| 7 | violet | 493.88 ÷ 32 = | 15.4 | violet |

When used in the electromagnetic application, the CD's can be recorded alternating the square wave (directed to the specific pathogen) and one or more of the chakra frequencies. For example, if a person was treating ulcers, a CD having a square wave frequency sweep of 727 to 880 would be alternated with the frequencies for the third and seventh chakras. The square wave would destroy the pathogens for a predetermined period of time and the chakra frequencies would subsequently balance and stimulate the healthy tissue in congruent areas. In many instances it is beneficial to stimulate not only the chakra directly involved with the disorder, but adjacent chakra(s). This determination will be apparent to those knowledgeable in the art.

The aforenoted incorporated publications have disclosed the frequencies previously found to destroy pathogens. Although most of Rife's disclosed frequencies are within the human hearing range, Clark's research used frequencies in the inaudible radio frequency range. It has now been found that there are key formulas which show the inter relationship of Rife's known frequencies regarding odd harmonics. These formulas tie the destructive frequencies for a particular pathogen to the odd harmonics, while the fundamental (F) frequencies set off a chain reaction of cascading odd harmonics which, in turn, destroy the pathogens. The square waves used in prior research generate the odd harmonics. It is these sine waves which destroy the pathogens. It is critical, however, that the initial frequency is in the form of a square wave. The frequency transfer unit shapes the recorded square waves and regulates the voltage, making the recorded protocols viable. Without the frequency transfer unit in line between the amplifier and user, the wave is distorted and the amplitude too high for human application. The set up CD allows the user to adjust the proper volume to shape the optimum wave form, and therefore optimal efficacy.

Table II sets forth the mathematical formulas correlating the harmonic interrelationship between Rife's known square wave frequencies.

TABLE II

| | F = Fundamental frequency |
|---|---|
| A | F × 2 = 2nd harmonic |
| B | F × 2.9965 = 3rd harmonic |
| C | F × 5.04 = 5th harmonic |
| D | (F × 15)7.945 = 7th note of the scale |
| E | F × 15 = 7th harmonic (attenuated −5.5) |
| F | F ÷ 2.9965 = 4th note of scale 2 octaves below fundamental |
| G | F ÷ 5.04 = augmented 5th 3 octaves below fundamental |
| H | F ÷ 15 = fundamental sharp 3 octaves below fundamental |

The multiplier of 15 is used since any frequency multiplied by 15 equals the 7th harmonic −5.5%, by frequency. This is a naturally occurring sequence of harmonics. Using Rife's frequencies, a number of tested frequencies were mathematically computed to determine whether another known frequency was obtainable. The following examples have been randomly selected. When the formula does not reveal the exact target, as indicated by placing the exact target in the target column.

TABLE III

| Known Fundamental Frequency | Formula | Harmonic Relationship Known Fundamental | Target |
|---|---|---|---|
| 1 | × [C] 5.04 = | 5.04 | 5 |
| 8 | × [D] 15 ÷ 7.946 = | 15.10 | 15 |
| 14 | × [B] 2.9965 = | 41.9 | 41 |
| 125 | × [C] 5.04 = | 600 | 625 |
| 240 | × [D] 15 ÷ 7.946 = | 453 | 450 |

When viewing Rife's chart illustrating the frequencies used to destroy specific pathogens, many of the frequencies disclosed therein are identical, and it is unlikely that the same frequencies disrupt the molecular structure of so many pathogens.

Clark has disclosed that radio frequencies serve to disrupt the molecular bonds of the pathogens. By applying the disclosed formulas (Table II), the harmonics used by Clark's radio frequencies can be taken to the audible range, matching those used by Rife's square wave audible frequencies, when divided by 100. Due to energy pooling, also known as forced resonance, a wave having sufficient amplitude and proximity to another wave will force congruity. Thus, a square wave with sufficient amplitude will generate sine waves cascading, at odd harmonic frequencies, i.e. 3-5-7-9 etc., at increasingly higher energy states. Along this path, all pathogens with frequencies of similar wave length will be forced to align themselves with the harmonic frequency, thus affecting any pathogens residing at "adjacent" frequencies.

Thus, the harmonics created at 664 hertz will destroy the pathogens not only in the "direct line" with 664 hertz, but will also force resonance of any pathogens residing at 660 and 666 hertz to align with 664 hertz, hence also being destroyed.

The disclosed system can also be used for stimulation and relaxation of various tissues. The prerecorded frequencies can be used in conjunction with the aforementioned frequencies or applied separately. Some of the novelty of the disclosed invention lies in the application of these frequencies to an easily used medium. Prior to the instant disclosure, these frequencies were generated by complex machines. In order, however to place the frequencies onto an easy to use recording medium, the frequency must first be generated by a frequency generator. These frequencies are recorded onto a CD and then, preferably, played back to ensure accuracy. Although the sine waves are pleasant to the human ear, the square waves are not and therefore square waves must be transmitted to the body through the use of electrodes. Sine waves can be recorded in conjunction with the square waves, with the waves being separated by the frequency transfer unit. Thus square waves would be directed to the electrodes and the sine waves directed to the earphones.

Since other modifications and changes varied to fit particular operating requirements and environments will be apparent to those skilled in the art, the invention is not considered limited to the example chosen for the purposes of disclosure, and covers all changes and modifications which do not constitute departures from the true spirit and scope of this invention.

What is claimed is:

1. A method of treating a body of a living being comprising the step of applying to said body a voltage in the form of a pathogen-specific square wave frequency recorded and applied synchronously with at least one Chakra frequency.

2. The method claim 1 further comprising a transfer system for modulating said square wave frequencies from a data storage medium, said system having a transmission member, at least one feed line, a transfer unit, an anode lead terminating at a first electrically conductive contact surfaces, a cathode lead terminating at a second electrically conductive contact surface and a voltage indicator activated at a predetermined minimum voltage, said at least one data storage medium having a setup transmission mode and multiple frequency modes, comprising the steps of:
activating said set up transmission mode,
adjusting said transmission member to output said predetermined minimum voltage and activate said voltage threshold indicator,
ceasing said set up transmission mode,
activating one of said multiple frequency modes,
placing said first contact surface adjacent a user's skin,
placing said second contact surface proximate a user's skin,
maintaining said frequency for a predetermined period of time,
wherein electrons generated by said square wave frequencies enter a user's body at said second contact surface and are attracted to said first contact surface, thereby conducting said electrons through a user's body.

3. The method of claim 2 wherein transmission member is a CD player and an amplifier and said data storage medium is a CD, said set up transmission mode and said multiple frequency modes being recorded on said CDs.

4. The method of claim 2 further comprising the step of adjusting the maximum voltage received by said contact surfaces using a set switch, said set switch being within said transfer unit and enabling a user to change the voltage output from said transfer unit.

5. The method of claim 1, further comprising at least one sine wave frequency recorded and applied in conjunction with said square wave frequency, wherein said at least one sine wave frequency is pleasant to a human ear.

6. The method of claim 5 wherein said sine wave frequency is transmitted to the body via earphones.

7. A method of stimulating and relaxing body tissue of a living being comprising the step of applying to said body a voltage in the form of a square wave frequency recorded and applied synchronously with at least one Chakra frequency and at least one sine wave frequency.

* * * * *